United States Patent
Hori et al.

(10) Patent No.: US 11,976,179 B2
(45) Date of Patent: May 7, 2024

(54) PARTICLE MATERIAL AND MANUFACTURING METHOD THEREFOR, AND TRANSPARENT RESIN COMPOSITION

(71) Applicant: ADMATECHS CO., LTD., Miyoshi (JP)

(72) Inventors: Kenta Hori, Miyoshi (JP); Takeshi Yanagihara, Miyoshi (JP); Sachie Nagano, Miyoshi (JP); Susumu Abe, Miyoshi (JP); Yuji Oono, Miyoshi (JP); Haruka Katsurayama, Miyoshi (JP)

(73) Assignee: ADMATECHS CO., LTD., Miyoshi (JP)

( * ) Notice: Subject to any disclaimer, the term of this patent is extended or adjusted under 35 U.S.C. 154(b) by 431 days.

(21) Appl. No.: 17/005,619

(22) Filed: Aug. 28, 2020

(65) Prior Publication Data

US 2020/0399441 A1 Dec. 24, 2020

Related U.S. Application Data (63) Continuation of application No. PCT/JP2019/008389, filed on Mar. 4, 2019.

(30) Foreign Application Priority Data

Mar. 2, 2018 (WO) .................. PCT/JP2019/008389

(51) Int. Cl.
| | | |
|---|---|---|
| *C08K 9/06* | (2006.01) | |
| *C08K 3/22* | (2006.01) | |
| *C08K 3/36* | (2006.01) | |
| *C08K 5/54* | (2006.01) | |
| *C08K 9/02* | (2006.01) | |

(52) U.S. Cl.
CPC .................. *C08K 9/06* (2013.01); *C08K 3/22* (2013.01); *C08K 3/36* (2013.01); *C08K 5/5403* (2013.01); *C08K 9/02* (2013.01); C08K 2003/2227 (2013.01); C08K 2201/006 (2013.01); C08K 2201/011 (2013.01)

(58) Field of Classification Search
CPC ... C08K 9/06; C08K 3/22; C08K 3/36; C08K 5/5403; C08K 9/02; C08K 2003/2227; C08K 2201/06; C08K 2201/011; C08K 2201/005; A61K 6/831; H01L 23/31; H01L 23/29; C01F 7/02; C08L 101/00; C09D 7/61; C09D 201/00; H05K 5/02

USPC ........................................................ 523/212
See application file for complete search history.

(56) References Cited

U.S. PATENT DOCUMENTS

| | | | |
|---|---|---|---|
| 7,491,440 B2 | 2/2009 | Fukatani et al. | |
| 2004/0010114 A1* | 1/2004 | Ozawa ................... | C08J 9/0004 528/367 |
| 2006/0110593 A1 | 5/2006 | Fukatani et al. | |
| 2015/0362631 A1 | 12/2015 | Ueno | |

FOREIGN PATENT DOCUMENTS

| | | |
|---|---|---|
| JP | H04305052 A | 10/1992 |
| JP | 2006219356 A | 8/2006 |
| JP | 2007154026 A | 6/2007 |
| JP | 2007154159 A | 6/2007 |
| JP | 2009221350 A | 10/2009 |
| JP | 2011251906 A | 12/2011 |
| JP | 2013142145 A | 7/2013 |
| WO | WO-2014132624 A1 | 9/2014 |

OTHER PUBLICATIONS

Written Opinion issued May 7, 2019 in PCT/JP2019/008389 (with English translation), 12 pages.
International Search Report issued May 7, 2019 in PCT/JP2019/008389 filed Mar. 4, 2019 (with partial English translation), 4 pages.
Office Action issued Apr. 23, 2020 in Japanese Patent Application No. 2020-503669 (with English translation), 8 pages.
Office Action issued Mar. 19, 2020 in Japanese Patent Application No. 2020-503669 (with English translation), 12 pages.

* cited by examiner

*Primary Examiner* — Hannah J Pak
(74) *Attorney, Agent, or Firm* — Element IP, PLC (57) ABSTRACT

Provided is a particle material that achieves excellent mechanical properties and optical properties when dispersed in a transparent resin material in order to solve the problem. In a case where primary particles having particle sizes in a certain range are formed into an aggregate, mechanical properties are enhanced while optical properties are maintained. The primary particles each have compositions different between the inside thereof and the surface thereof. Therefore, the optical properties to be obtained are easily controlled unlike an inorganic substance in which both of the compositions are mixed at an atomic level. The particle material of the present invention is an aggregate including primary particles in which a specific surface area. diameter is not less than 0.8 nm and not greater than 80 nm, the primary particles formed of an inorganic substance in which a composition of a surface and a composition of an inside are different.

16 Claims, 6 Drawing Sheets

| Sintering Temperature | Material | 2θ | FWHM | 2θ | FWHM | 2θ | FWHM | 2θ | FWHM | 2θ | FWHM | 2θ | FWHM | Refractive Index |
|---|---|---|---|---|---|---|---|---|---|---|---|---|---|---|
| Comparative Example 1-0 | | 38.361 | 1.63 | | | 49.083 | 1.63 | 64.855 | 0.87 | 67.013 | 2.18 | 71.962 | 1.855 | 1.59 |
| Comparative Example 1-5 | Boehmite | 38.3 | 1.5 | 45.8 | 0.9 | 49.2 | 1.6 | 64.8 | 1.5 | | | 72.2 | 1.7 | 1.60 |
| Comparative Example 1-6 | γ Alumina | 38.5 | 3.8 | 45.8 | 4.6 | | | | | 66.8 | 3.8 | 72.0 | 2.4 | 1.63 |
| Comparative Example 1-7 | γ Alumina | 38.4 | 4.0 | 45.7 | 3.7 | | | | | 66.9 | 3.5 | 72.1 | 2.3 | 1.65 |
| Example 1-0 | | 38.1 | 1.9 | | | 49.1 | 1.6 | 64.9 | 0.9 | 66.9 | 2.0 | 72.1 | 1.8 | 1.56 |
| Example 1-5 | Boehmite | 38.3 | 1.8 | | | 49.3 | 1.5 | 65.0 | 0.7 | 67.0 | 1.9 | 72.1 | 1.9 | 1.56 |
| Example 1-6 | Boehmite | 38.3 | 1.7 | 45.9 | 2.4 | 49.2 | 2.2 | 64.5 | 2.1 | | | 72.1 | 1.8 | 1.55 |
| Example 1-7 | Boehmite | 38.2 | 2.0 | 45.9 | 1.5 | 49.5 | 1.1 | 64.8 | 1.9 | | | 72.1 | 1.9 | 1.55 |
| | | Boehmite | | γ Alumina | | Boehmite | | Boehmite | | γ Alumina | | Boehmite | | |

Fig. 6

PARTICLE MATERIAL AND MANUFACTURING METHOD THEREFOR, AND TRANSPARENT RESIN COMPOSITION

CROSS REFERENCE TO RELATED APPLICATIONS

The present application is a Continuation Application of international Application No. PCT/JP2019/008389, filed on Mar. 4, 2019, which is incorporated herein by reference. The present invention is based on International Application No. PCT/JP2018/008060, filed on Mar. 2, 2018, the entire contents of which are incorporated herein by reference.

BACKGROUND OF THE INVENTION

1. Field of the Invention

The present invention relates to a particle material and a manufacturing method for the particle material, and a transparent resin composition.

2. Description of the Related Art

To date, a transparent resin composition in which a particle material formed from an inorganic material is dispersed has been manufactured in order to improve mechanical properties of a transparent resin material. The obtained transparent resin composition has high mechanical properties.

As one of means for improving mechanical properties of a transparent resin composition, means for increasing particle sizes of particle materials in order to improve mechanical properties of the particle materials to be dispersed, or means for varying the kind of inorganic material of a particle material is used.

Furthermore, as means for changing optical properties for achieving required optical properties, means for varying the kind of particle material, or means for changing a material to a material having different optical properties or mixing materials having different optical properties is used.

CITATION LIST

Patent Literature

Patent Literature 1: JP2009-221350 (A)
Patent Literature 2: JP2006-219356 (A)
Patent Literature 3: JP2007-154159 (A)
Patent Literature 4: JP2011-251906 (A)

SUMMARY OF THE INVENTION

However, in a case where, in order to increase particle sizes for improving mechanical properties, the particle sizes of the particle material are made too large to be ignored with respect to an assumed light ray wavelength, a haze value increases and light transmissivity decreases.

In a case where materials having different optical properties are used, sufficient mechanical properties are not exhibited, or dispersion in a transparent resin material is not sufficient depending on the kind of inorganic material, in some cases.

Patent Literature 1 to Patent Literature 3 represent conventional art in which inorganic particles having small particle sizes are contained. Patent Literature 1 discloses a manufacturing method for manufacturing a resin composition that contains, in resin, inorganic oxide particles having core-shell structures. According to Patent Literature 1, a refractive index is appropriately controlled by using the inorganic oxide particles having the core-shell structures, and, furthermore, fusing of particles as the inorganic oxide particles having the core-shell structures is inhibited (the first sentence in paragraph 0012 in Patent Literature 1). Therefore, in the inorganic oxide particles having the core-shell structures in Patent Literature 1, even in a case where the particles aggregate, the particles easily disperse again. Furthermore, according to Patent Literature 1, heating at a temperature of not lower than 250° C. at which boehmite dehydrates to cause transition to alumina is suggested (paragraph 0024 in Patent Literature 1).

Patent Literature 2 discloses a technique in which inorganic oxide particles having core-shell structures are contained in a transparent resin material. In Patent Literature 2, the to-be-contained inorganic oxide particles which have the core-shell structures are dried at, a temperature between a low temperature and normal temperature as described in paragraph 0067 in Patent Literature 2, and, even in a case where the particles aggregate, the particles easily disperse again.

Patent Literature 3 discloses a composite oxide formed by silicon oxide and metal oxide of one or more metals other than silicon, and also discloses inorganic oxide particles having core-shell structures. As disclosed in paragraph 0018 in Patent Literature 3, preferably, the inorganic oxide particles each disperse as an individual particle (primary particle). However, unavoidable aggregates are assumed to be contained. The particle diameter D50 is defined as being not greater than 30 nm, and a peak value (Dp) in a frequency distribution function of a distance between particles is defined as being not greater than 30 nm, and the degree of aggregation is required to be very small as is seen from the values of D50 and by which are almost the same.

In Example in Patent Literature 3, an inorganic fine particle C corresponds to an inorganic oxide particle having a core-shell structure, and is dried at 190° C. which is a temperature lower than a temperature for dehydration and condensation. An inorganic fine particle D is dried at 450° C. In the process of manufacturing the inorganic fine particle D, an organic silane coupling agent is caused to react with zirconia oxide powder, and treatment with tetraethoxysilane is thereafter performed, to manufacture a composite particle in which zirconia oxide and silica are mixed in a mosaic manner, instead of a particle having a core-shell structure, and heating at 450° C. is thereafter performed to form a composite oxide of zirconia and silica.

The present invention has been completed in view of such circumstances, and an object of the present invention is to provide a particle material that achieves mechanical properties and optical properties different from those in conventional it when dispersed in a transparent resin material, a manufacturing method for the particle material, and a transparent resin composition using the particle material, in order to solve the problem.

In order to solve the aforementioned problem, the inventors of the present invention have found, as a result of thorough investigation, that, in a case where primary particles having particle sizes in a certain range are formed into an aggregate, mechanical properties are enhanced while maintaining optical properties, as compared with a case where the particle sizes simply increase, and, furthermore, in a case where the primary particles are structured to have inorganic material compositions different between the inside thereof and the surface thereof, an inorganic material which has been difficult to adopt mainly for a reason other than optical properties is allowed to be contained. Specifically, the inventors have found that a structure in which the composition of the inside is γ alumina or boehmite and the surface contains silica is advantageous. Furthermore, the inventors have found that, since the composition of the surface and the composition of the inside are set independently, the optical properties to be obtained are easily controlled unlike an inorganic substance in which both of the compositions are mixed at an atomic level. The aggregate is obtained by binding and fusing particles through dehydration and condensation, thereby enhancing strength of particles. Because of binding and fusing the primary particles, the particle size of the primary particle is defined as a specific surface area diameter based on a surface communicating with the outside, instead of the particle size or the primary particle being directly defined. That is, gaps between the primary particles are filled with a material (corresponding to a transparent resin for the transparent resin composition) that forms a matrix in the case of the composition being formed. Therefore, for the optical properties, influence of the sizes of the primary particles increases.

Specifically, in order to achieve the aforementioned object, a particle material of the present invention is an aggregate including primary particles in which a specific surface area diameter based on a surface communicating with outside is not less than 0.8 am and not greater than 80 nm, the primary particles formed of an inorganic substance in which a composition of a surface and a composition of an inside are different from each other, the aggregate being formed by binding and fusing particles through dehydration and condensation.

A manufacturing method for manufacturing a particle material for achieving the aforementioned object is a manufacturing method for manufacturing the above-described particle material, and the manufacturing method includes: a dispersing step of dispersing, in a liquid dispersion medium, particles having a composition of the inside to form a dispersion liquid; a coating step of dissolving a precursor having a composition of the surface in the dispersion liquid, and thereafter transforming the precursor to the composition of the surface, to coat the core particles and form coated particles; and an aggregating step of forming an aggregate by heating the coated particles, and subjecting the coated particles to dehydration and condensation to bind and fuse particles.

In order to achieve the aforementioned object, a transparent resin composition includes: the above-described particle material; and a transparent resin material in which the particle material is dispersed, and a light transmittance (400 nm/2 in is not less than 80%.

The composition of the surface and the composition of the inside are made different, whereby an effect of providing a particle material with advantageous properties when dispersed in a transparent resin material is obtained.

DESCRIPTION OF THE EMBODIMENTS (Particle Material)

A particle material of the present invention will be described below in detail based on an embodiment. The particle material of the present embodiment is a material which allows a transparent resin composition obtained by dispersing the particle material in a transparent resin material to have high optical properties. Furthermore, the particle material of the present embodiment has properties that have not been achieved by conventional art, in addition to the optical properties. Examples of the properties obtained when the particle material of the present embodiment is dispersed in another material as in a transparent resin composition or the like include a high transparency, a low coefficient of thermal expansion (CTE), a high gas barrier property, a high elastic modulus, a high surface hardness, a high compression strength, and a high antiblocking property. These performances are achieved by the contained particle material.

The particle material of the present embodiment is an aggregate in which primary particles are bound and fused by dehydration and condensation. The particle sizes in the aggregate are not particularly limited. By binding and fusing the primary particles, binding the primary particles is made strong to enhance mechanical strength of the particle material, unlike in Patent Literature 1 to Patent Literature 3. The larger the particle size is, the higher the strength becomes. Therefore, the particle size is preferably increased to a degree to which the particles are mixed. For example, in the case of application to thin film or the like which the particle material is unlikely to physically enter, the particle size distribution of the particle material is appropriately determined such the particle material physically enters the structure of the applied portion.

A preferable lower limit value of a volume average particle diameter is, for example, 0.1 μm, 0.5 μm, and 1.0 μm. A preferable upper limit value of the volume average particle diameter is, for example, 500 μm, 100 μm, 10 μm, and 5 μm. Furthermore, peaks appear at a plurality of particle sizes such as a large particle size and a small particle size.

In the particle material of the present embodiment, a specific surface area diameter based on a surface communicating with outside air is not less than 0.8 nm and not greater than 80 nm. The specific surface area diameter indicates a value calculated from a specific surface area (a surface area per unit mass) and a specific gravity of a material of the particle material. For a secondary particle formed as the aggregate of the primary particles, a value close to the particle size of the primary particles that form the secondary particle is calculated.

The lower limit value of the specific surface area diameter is 1 nm, 5 nm, or 10 nm. The upper limit value of the specific surface area diameter is 30 nm, 50 nm, or 70 nm.

The primary particles (hereinafter, referred to as "constituent primary particles" as appropriate) of the aggregate are formed of an inorganic substance in which a composition of the surface and a composition of the inside are different from each other. In a case where the composition of the surface and the composition of the inside are different, influence of a material of the inside on the outside is reduced in the constituent primary particles. The influence from the outside on the inside is also reduced. An unexpected effect is exhibited by interaction between the composition of the surface and the composition of the inside in some cases. For example, the unexpected effect is an effect that, in a case where γ alumina is used as the composition of the inside and the surface is formed of another material (for example, silica), an influence is exerted on phase transition of crystals of γ alumina. Occurrence of phase transition of γ alumina by heating is known. However, γ alumina in the constituent primary particles in which the surface is formed of a different material is confirmed to cause no phase transition even if heated up to a temperature at which γ alumina solely causes the phase transition. Therefore, the aggregate is manufactured by dehydration and condensation at a temperature of not lower than 900° C. (preferably not lower than 950° C., not lower than 1000° C.)

In a case where boehmite is used as the composition of the inside and silica is used for the surface, transition from boehmite to alumina (in particular, γ alumina) by heating is inhibited. Therefore, the aggregate is manufactured by dehydration and condensation at a temperature of higher than 250° C.

As long as such constituent primary particles are a main component, a primary particle having another composition (for example, the entirety thereof is formed of a single composition) is allowed to be contained. In the description herein, the "main component" means that 50% or more by mass of the component is contained, 70% or more by mass thereof is preferably contained, and 90% or more by mass thereof is more preferably contained. Other than the constituent primary particles, a particle which is allowed to be contained as the primary particle is, for example, a second particle formed of oxide of an element having an atomic number of 38 or higher. Preferable specific examples of the contained element that has an atomic number of 38 or higher and is contained in the oxide include zirconium. The shape of the constituent primary particle is not particularly limited.

In the constituent primary particles, a composition of an inorganic substance is optionally selected for each of the composition of the surface and the composition of the inside. As the composition of the surface, silica is preferably selected. Various surface treatments are easily performed with silica on the surface, and silica has both high physical stability and high chemical stability and is easily synthesized. From the viewpoint of enhancement of optical properties, amorphous silica is preferably used.

A ratio between the surface and the inside is not particularly limited. The surface preferably covers the inside with no substantial gaps.

The particle material of the present embodiment is allowed to have, on the surface, a coating layer formed of an organic substance. The coating layer covers the surfaces of the constituent primary particles. Although the thickness of the coating layer is not particularly limited, the coating layer preferably covers the surface of the particle material with no substantial gaps. In a case where the coating layer is formed, the coating layer is disposed between the aggregated constituent primary particles, or the coating layer covers the surfaces of the aggregated constituent primary particles to cover the constituent primary particles that are directly aggregated. The coating layer preferably binds to the surfaces of the constituent primary particles through covalent bond or physically binds to the surfaces of the constituent primary particles by an intermolecular force or the like. The organic substance of the coating layer is preferably a condensation product of a silane compound. In a case where the silane compound has two or more SiOR, the coating layer formed of a condensation product is obtained. As a method for manufacturing a condensation product of the silane compound, a method for condensing the above-described silane compound in a state where the silane compound is in contact with the surfaces of the constituent primary particles (either before or after the aggregate is formed) is used. The constituent primary particles are formed of an inorganic material, and the surfaces of the constituent primary particles contain an OH-group in general. Therefore, the above-described silane compound reacts with the OH-group in the surfaces of the constituent primary particles to form a covalent bond.

In the particle material of the present embodiment, in a case where $Al_2O_3$ is used for the composition of the surface or the inside, the half-value width of a peak appearing at 2θ of each of 45° to 49° and 64° to 67° in X-ray diffraction is preferably not less than 0.5°. A peak (first peak) in the range where 2θ is 45° to 49° represents γ alumina, and a peak (second peak) in the range where 2θ is 64° to 67° represents γ alumina. In a case where the half-value width of a peak in each of these ranges is not less than 0.5°, α alumina is not generated and the particle material is preferable.

Furthermore, in the particle material of the present embodiment, in a case where boehmite is used for the composition of the surface or the inside, the half-value width of a peak appearing at 2θ of each of 37° to 39° and 71° to 73° in X-ray diffraction is preferably not greater than 2.5°, and/or the half-value width of a peak appearing at 2θ of each of 45° to 49° and 64° to 67° is preferably not greater than 2.5°. A peak in each of these ranges of 2θ represents boehmite. In a case where the half-value width of the peak in each of these ranges is not greater than 2.5°, boehmite remains and the particle material is preferable.

(Manufacturing Method for Particle Material)

The manufacturing method for the particle material according to the present embodiment is a method for preferably manufacturing the above-described particle material. The manufacturing method for the particle material according to the present embodiment includes a dispersing step, a coating step, and other steps selected as necessary. Examples of the other steps include an aggregating step, a modifying step, and a particle size distribution adjusting step.

In the dispersing step, particles (core particles) having the composition of the inside are dispersed in a liquid dispersion medium to obtain a dispersion liquid. The core particles are obtained in a general method. For example, reaction of a compound as a precursor of the composition or the inside is caused to manufacture the core particles. For example, in a case where boehmite is used as the composition of the inside, aluminium hydroxide having appropriate particle sizes through pulverization or the like is used as the precursor and is subjected to hydrothermal treatment, to obtain core particles formed of boehmite. Furthermore, aluminium oxide having appropriate particle sizes is used as the precursor and is heated in acid or alkali aqueous solution to obtain the core particles.

In the coating step, colloidal silica or a precursor as a compound to be formed into a composition of the surface through reaction is added to the obtained dispersion liquid to generate the composition of the surface, and the surfaces of the core particles are coated with the composition of the surface, thereby forming coated particles. A ratio between the composition of the inside and the composition of the surface is controlled according to an amount of the precursor to be added. Any compound is used as the precursor. In a case where silica is used as the composition of the surface, tetraethoxysilane is used as the precursor. Silica is easily generated by tetraethoxysilane in the presence of water. For example, a so-called sol-gel process in which tetraethoxysilane is hydrolyzed in an acidic or basic atmosphere is used. The colloidal silica is adhered to the surfaces of the core particles and aggregated in the aggregating step described below to form silica as "the composition of the surface".

The aggregating step is performed after the coating step. In the aggregating step, the coated particles obtained in the coating step are heated and aggregated. The obtained aggregate is allowed to be pulverized or classified so as to obtain a required particle size distribution. The heating temperature in the aggregating step is a temperature at which dehydration and condensation occur in the coated particles. The heating temperature is, for example, higher than 250° C., not lower than 450° C., or not lower than 500° C. The particle material obtained by heating in these temperature ranges has enhanced strength.

The modifying step is performed after the coating step. In the modifying step, a silane compound is brought into contact with the surfaces of the coated particles obtained in the coating step to perform modification. In a case where the modifying step and the aggregating step are performed in combination, the modifying step is performed before or after the aggregating step.

(Transparent Resin Composition)

The transparent resin composition of the present embodiment includes the above-described particle material and a transparent resin material in which the particle material is dispersed. The transparent resin composition of the present embodiment preferably has a light transmittance of not less than 80%, and particularly preferably has a light transmittance of not less than 85% and of not less than 90%. The light transmittance is measured with a light ray having a wavelength of 400 nm by using a test sample having a thickness of 2 mm. A mixing ratio between the particle material and the transparent resin material is determined so as to achieve the above-described light transmittance. The proportion of the particle material is preferably increased from the viewpoint of enhancement of mechanical properties.

The particle material to be used is as described above, and the repeated description thereof is omitted. As the transparent resin material, a standard resin material such as thermoplastic resin and thermosetting resin is selected. Examples of the transparent resin material include epoxy resin, polyimide, polycarbonate, polyethylene terephthalate, polybutylene terephthalate, polymethylmethacrylate, vinyl chloride, polypropylene, and polyethylene.

A method for dispersing the particle material in the transparent resin material is not particularly limited. For example, in a case where the thermoplastic resin is used as the transparent resin material, a heated and melted transparent resin material and the particle material are mixed and kneaded, or a precursor (transparent resin precursor material: monomer or the like) of the transparent resin material and the particle material are mixed and thereafter polymerized, to obtain the transparent resin composition. In a case where the transparent resin material is thermosetting resin, a precursor (monomer, prepolymer, or the like) of the transparent resin material and the particle material are mixed and thereafter hardened.

A photopolymerizable transparent resin composition is provided by using a photopolymerizable material as the transparent resin precursor material. The photopolymerizable transparent resin composition is used for manufacturing a molded product by the photopolymerizable transparent resin composition being enclosed in a mold and light rays being then applied, or is used as a photocurable resin material for fabrication by a so-called stereolithography type 3D printer. The polymerized resin composition is expected to have a high transparency, a low coefficient of thermal expansion (CTE), and a high elastic modulus.

EXAMPLES

The particle material, the manufacturing method for the particle material, and the transparent resin composition according to the present invention will be described below in detail based on examples.

(Test 1: Manufacturing a Particle Material as an Aggregate Formed from Primary Particles in a Case where Silica used as a Composition of the Surface and Boehmite is used as a Composition of the Inside)

40 parts by mass of isopropanol (IPA) was added to 100 parts by mass of Alumisol-10A (containing 10% by mass of $Al_2O_3$: width×length was 10 nm×50 nm: corresponding to core particles) manufactured by Kawaken Fine Chemicals Co., Ltd., and 10 parts by mass of tetraethoxysilane (TEOS: precursor of silica as the composition of the surface) was added. A mass ratio between boehmite and silica in the finally obtained particle material was theoretically 78:22 by adopting the mixing ratio.

A gel precipitate formed of the constituent primary particles was obtained through reaction at room temperature for 24 hours and neutralization with ammonia water. The precipitate was washed by pure water, dried at 160° C. for two hours, and pulverized by a let mill so as to have a mean particle diameter of not greater than 2 μm, to obtain a particle material of example 1-0.

The particle material of example 1-0 was subjected to heat treatment at 650° C. for two hours to obtain a particle material of example 1-1. The particle material of example 1-0 was subjected to heat treatment at 850° C. for two hours to obtain a particle material of example 1-2.

Figure 1:
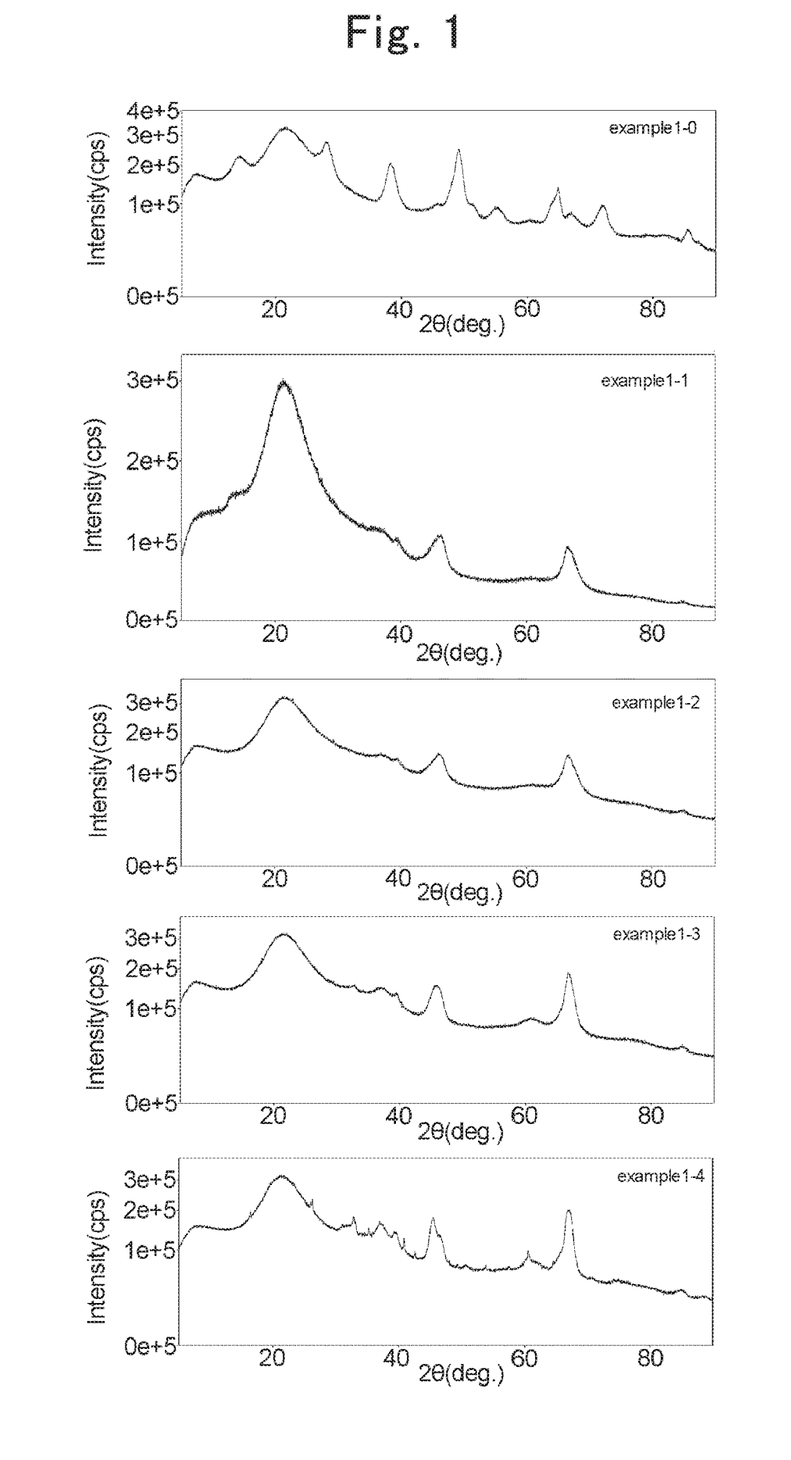
FIG. 1 illustrates an XRD spectrum of each sample in examples.
Figure 3:
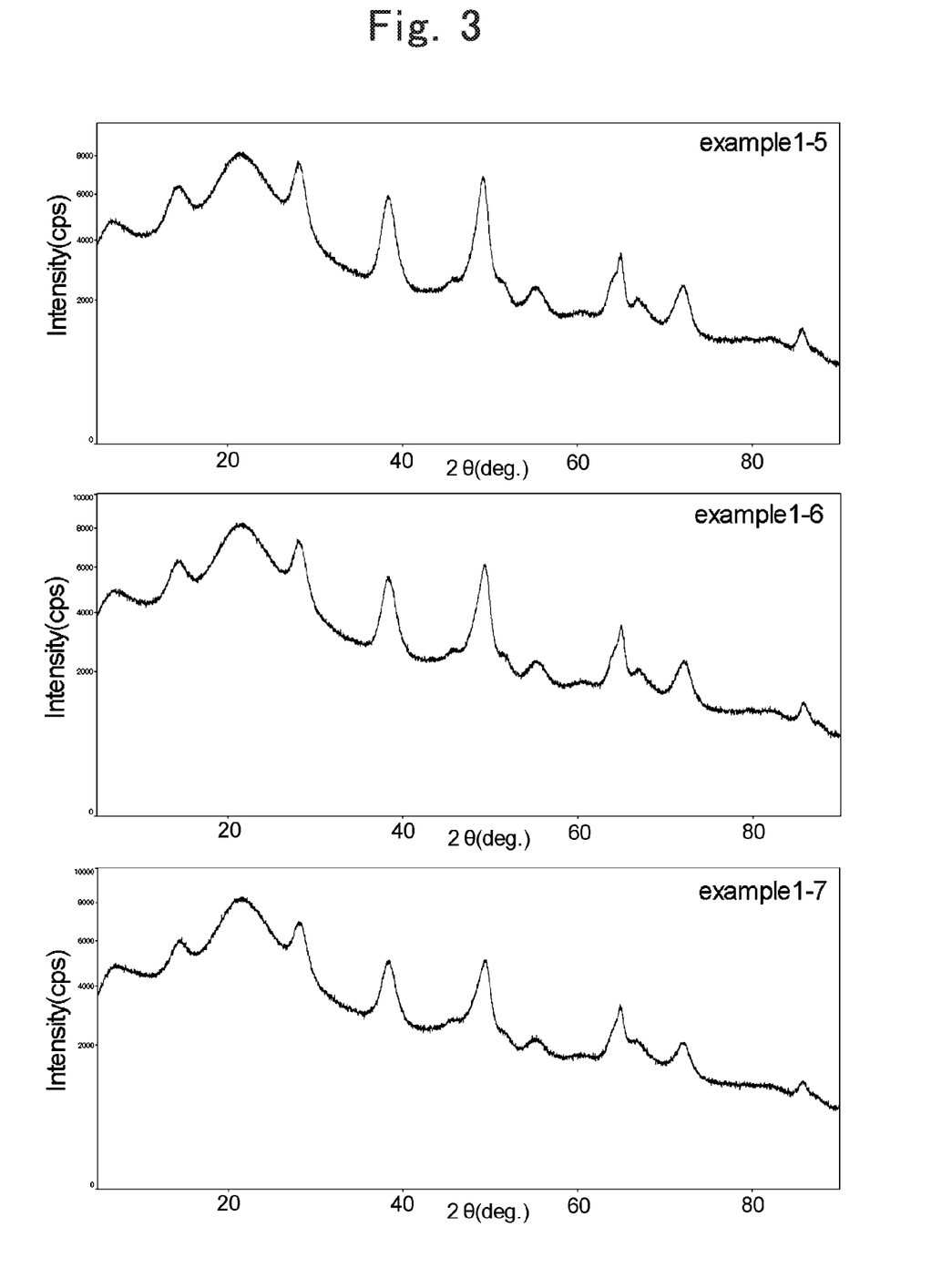
FIG. 3 illustrates an XRD spectrum of each sample in examples.

The particle material of example 1-1 was subjected to heat treatment at 1100° C. for two hours to obtain a particle material of example 1-3. The particle material of example 1-1 was subjected to heat treatment at 1200° C. for two hours to obtain a particle material of example 1-4. Furthermore, the particle material of example 1-0 was subjected to heat treatment at 250° C. (example 1-5), 400° C. (example 1-6), and 450° C. (example 1-7) for two hours to obtain a particle material of each example. Table 1 indicates the volume average particle diameter, the specific surface area, and the refractive index of the particle material of each of example 1-0 to example 1-7. The volume average particle diameter was measured by using a laser diffraction type particle size measuring device. The specific surface area was measured by a BET method using nitrogen. The refractive index of the particle was defined in the following method. A plurality of mixed solvents having different blending ratios between two kinds of solvents having known refractive indexes were prepared as references. A refractive index of a mixture having a transmittance of not less than 80% (589 nm/10 mm) and the highest transparency when the particles were dispersed in the mixed solvents was determined as the refractive index of the particle. The mixture having a transmittance of less than 80% was defined as being optically imperfectly opaque. FIG. 1 collectively shows an XRD spectrum of each of examples 1-0 to 1-4. FIG. 3 collectively shows an XRD spectrum of each of examples 1-5 to 1-7. Table 2 indicates the half-value width (FWHM) of a peak appearing at 2θ of each of 45° to 49° and 64° to 67° in each example as calculated from the result of each XRD measurement.

TABLE 1

| Example | Mean particle diameter (μm) | Specific surface area diameter (μm) | Specific surface area (m2/g) | Refractive index | Heating temperature (° C.) |
|---|---|---|---|---|---|
| 1-0 | 1.72 | 6.7 | 333.1 | 1.59 | 160 |
| 1-1 | 1.41 | 6.1 | 335.2 | 1.61 | 160-650 |
| 1-2 | 1.51 | 6.9 | 284.3 | 1.62 | 160-850 |
| 1-3 | 1.39 | 9.4 | 190.4 | 1.63 | 160-850-1100 |
| 1-4 | 1.38 | 21.8 | 74.9 | 1.63 | 160-850-1200 |
| 1-5 | 1.7 | 6.7 | 332 | 1.6 | 160-250 |
| 1-6 | 1.7 | 6.7 | 334 | 1.6 | 160-400 |
| 1-7 | 1.7 | 6.7 | 333 | 1.6 | 160-450 |

TABLE 2

| Example | 2θ | FWHM | 2θ | FWHM | Heating temperature (° C.) |
|---|---|---|---|---|---|
| 1-0 | 49.1 | 1.6 | 64.9 | 0.9 | 160 |
| 1-1 | 46.2 | 2.6 | 66.4 | 2.9 | 160-650 |
| 1-2 | 46.2 | 3 | 66.5 | 2.4 | 160-850 |
| 1-3 | 45.9 | 2.1 | 66.7 | 1.6 | 160-850-1100 |
| 1-4 | 45.4 | 1.1 | 66.9 | 1.4 | 160-850-1200 |
| 1-5 | 38.3 | 1.8 | 65 | 0.7 | 160-250 |
| 1-6 | 38.3 | 1.7 | 64.5 | 2.1 | 160-400 |
| 1-7 | 38.2 | 2 | 64.8 | 1.9 | 160-450 |

As is apparent from Table 1, the particle material of example 1-0 indicates a value close to a value (about 1.60) calculated from 1.65 as the refractive index of boehmite, 1.45 to 1.47 as the refractive index of silica, and a mixing ratio (78:22) between the boehmite and silica. The particle materials of examples 1-1 to 1-4 indicate high refractive indexes of 1.62 to 1.63 since transit ion of boehmite to γ alumina occurred by heating at a high temperature.

The result of the XRD measurement indicated that the half-value width of a peak appearing at 2θ of each of 45° to 49° and 64° to 67° was not less than 0.7 in each example, and generation of crystals derived from α alumina was not confirmed. In general, transition of boehmite to α alumina occurs by heating at about 1200° C. However, the result indicated that the transition to α alumina was inhibited by coating the surface with silica.

The specific surface area was constant and substantially slightly less than 340 m²/g in heating up to 650° C. in the examples, and the higher the heating temperature was, the greater the specific surface area diameter was in a case where the heating temperature was higher than that temperature (for example, in a case here the heating temperature was not lower than 850° C.), and sintering of the constituent primary particles was confirmed to progress, and the strength of the particle material was assumed to be enhanced.

(Test 2: Formation of a Coating Layer Formed of an Organic Substance: Case 1)

The particle material (dried at 160° C. and then sintered at 850° C.) of example 1-2 was put into a mixer at a blending amount indicated in Table 3, and, thereafter, a silane compound solution corresponding to a blending amount (an amount of silane compound) of the organic substance indicated in Table 3 was put in the mixer while being stirred, to perform surface treatment. The silane compound solution was a mixture in which vinyltrimethoxysilane (KBM-1003 manufactured by Shin-Etsu Chemical Co., Ltd.) as the silane compound, IPA, and water were mixed at the same amount.

Thereafter, the obtained product was aged at room temperature for one day as it was, and then heated at 160° C. for two hours to evaporate the liquid component, thereby obtaining a composite aggregate according to each of examples 2-1 to 2-3. A coating layer formed of the organic substance was formed on the surface of the particle material through the surface treatment.

TABLE 3

| | Specific surface area diameter (nm) | Example 1-2 (parts by mass) | Silane compound (parts by mass) | Retractive index |
|---|---|---|---|---|
| Example 1-2 | 7 | 100 | 0 | 1.62 |
| Example 2-1 | 7 | 100 | 10 | 1.59 |
| Example 2-2 | 7 | 100 | 40 | 1.54 |
| Example 2-3 | 7 | 100 | 50 | 1.52 |

As is apparent from Table 3, by increasing an amount of the silane compound to be processed, the thickness of the coating layer was increased, and the greater the thickness of the coating layer was, the less the refractive index was.

(Test 3: Formation of a Coating Layer Formed of an Organic Substance: Case 2)

The particle material (only dried at 160° C.) Of example 1-0 was put into a mixer at a blending amount indicated in Table 4, and, thereafter, a silane compound solution corresponding to a blending amount (an amount of silane compound) of the organic substance indicated in Table 4 was put in the mixer while being stirred, to perform surface treatment. The silane compound solution was a mixture in which vinyltrimethoxysilane (KBM-1003 manufactured by Shin-Etsu Chemical Co., Ltd.) as the silane compound, IPA, and water were mixed at the same amount.

Thereafter, the obtained product was aged at room temperature for one day at it was, and then heated at 160° C. for two hours to evaporate the liquid component, thereby obtaining a composite aggregate according to each of examples 3-1 to 3-3. A coating layer formed of the organic substance was formed on the surface of the particle material through the surface treatment.

TABLE 4

| | Specific surface area diameter (nm) | Example 1-0 (parts by mass) | Silane compound (parts by mass) | Refractive index |
|---|---|---|---|---|
| Example 1-0 | 6.4 | 100 | 0 | 1.59 |
| Example 3-1 | 6.4 | 100 | 10 | 1.58 |
| Example 3-2 | 6.4 | 100 | 50 | 1.57 |
| Example 3-3 | 6.4 | 100 | 100 | 1.56 |

As is apparent from Table 4, by increasing an amount of the silane compound to be added, the thickness of the coating layer formed of the organic substance was increased, whereby the refractive index was reduced.

(Test 4: Formation of a Coating Layer Formed of an Organic Substance: Case 3)

A particle material according to each of examples 4-1, 4-2, and 4-3 was manufactured in the same manner as in example 1-2 described above except that an amount of TEOS to be added was changed to the amount indicated in Table 5.

TABLE 5

| Example | Specific surface area diameter (nm) | Boehmite (parts by mass) | Blending amount of TEOS (parts by mass) | Refractive index | Boehmite:silica (theoretical ratio) |
|---|---|---|---|---|---|
| 1-2 | 7 | 100 | 10 | 1.62 | 78:22 |
| 4-1 | 7.7 | 100 | 20 | 1.56 | 63:37 |
| 4-2 | 8.1 | 100 | 30 | 1.54 | 54:46 |
| 4-3 | 7.7 | 100 | 685 | 1.43 | 5:95 |

The measured values of the refractive index indicated that the refractive index was controlled by increasing an amount of TEOS to be added.

Furthermore, 50 parts by mass of methyltrimethoxysilane (KBM-13 manufactured by Shin-Etsu Chemical Co., Ltd.) was caused to react with 100 parts by mass of the particle material according to each of examples 1-2, 4-1, 4-2, and 4-3 to obtain particle materials of examples 4-4, 4-5, 4-6, and 4-7, respectively, and the refractive index of each particle material was measured (Table 6).

TABLE 6

| Example | Specific surface area diameter (nm) | Blending amount of particle material (parts by mass) | Boehmite:TEOS (mass ratio) | Blending amount of methyl-trimethoxy-silane (parts by mass) | Refractive index | Boehmite:silica (theoretical ratio) |
|---|---|---|---|---|---|---|
| 4-4 | 7 | 100 | 100:10 | 50 | 1.54 | 78:22 |
| 4-5 | 7.7 | 100 | 100:20 | 50 | 1.5 | 63:37 |
| 4-6 | 8.1 | 100 | 100:30 | 50 | 1.49 | 54:46 |
| 4-7 | 7.7 | 100 | 100:685 | 50 | 1.42 | 5:95 |

As is apparent from Table 6, the refractive index was controlled by performing the surface treatment with KBM-13. The refractive index was made less than an original refractive index of the particle material through the treatment with KBM-13.

(Test 5: Case where a Layer Formed of Silica was not Formed on a Surface)

Particle materials were manufactured in the same manners as in examples 1-0 to 1-7 of Test 1 except that TEOS was not added, to obtain particle materials of comparative examples 1-0 to 1-7, respectively. The particle material of each comparative example was entirely formed of boehmite or formed of γ alumina generated by transition of boehmite by heating.

Figure 2:
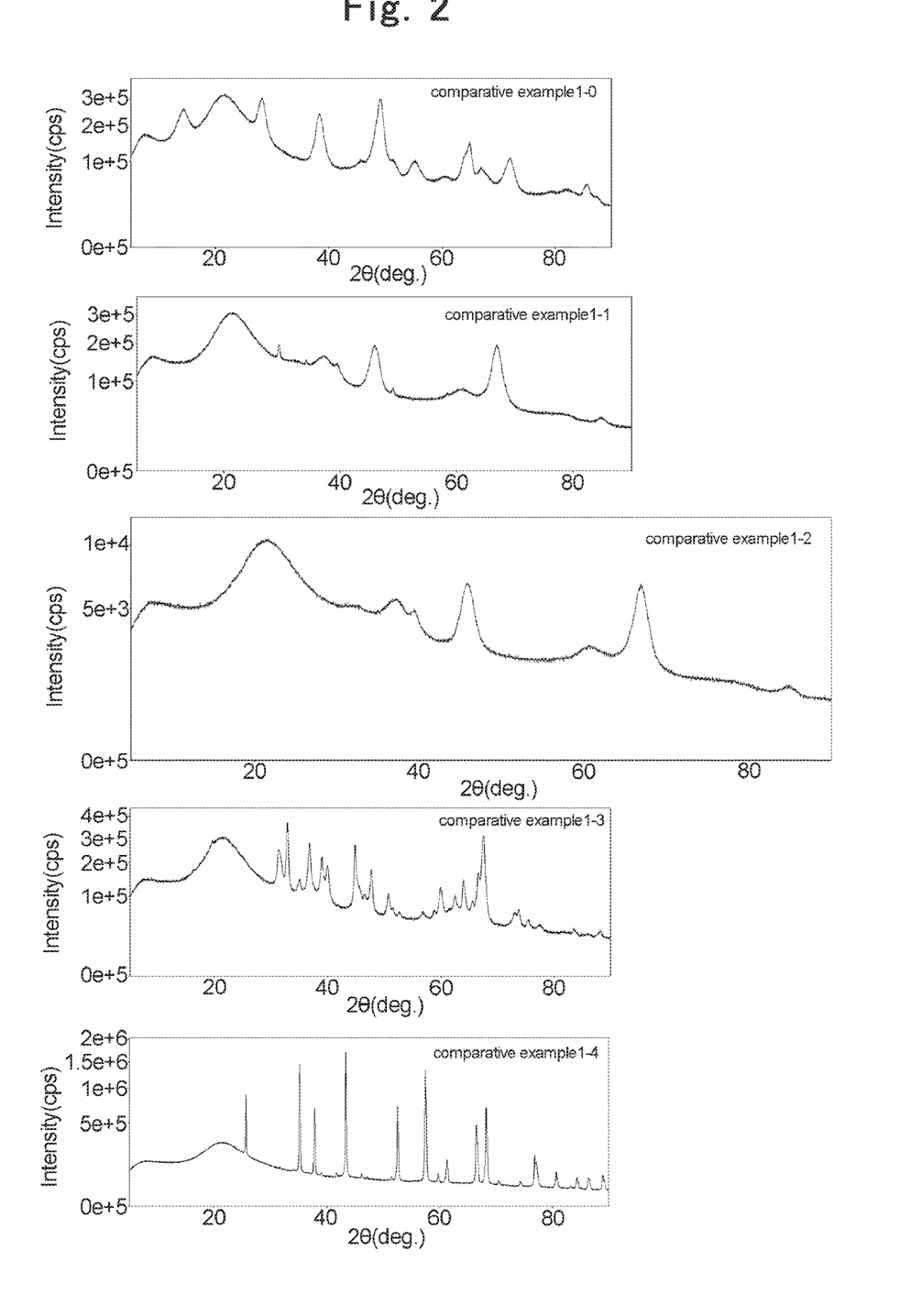
FIG. 2 illustrates an XRD spectrum of each sample in comparative examples.
Figure 4:
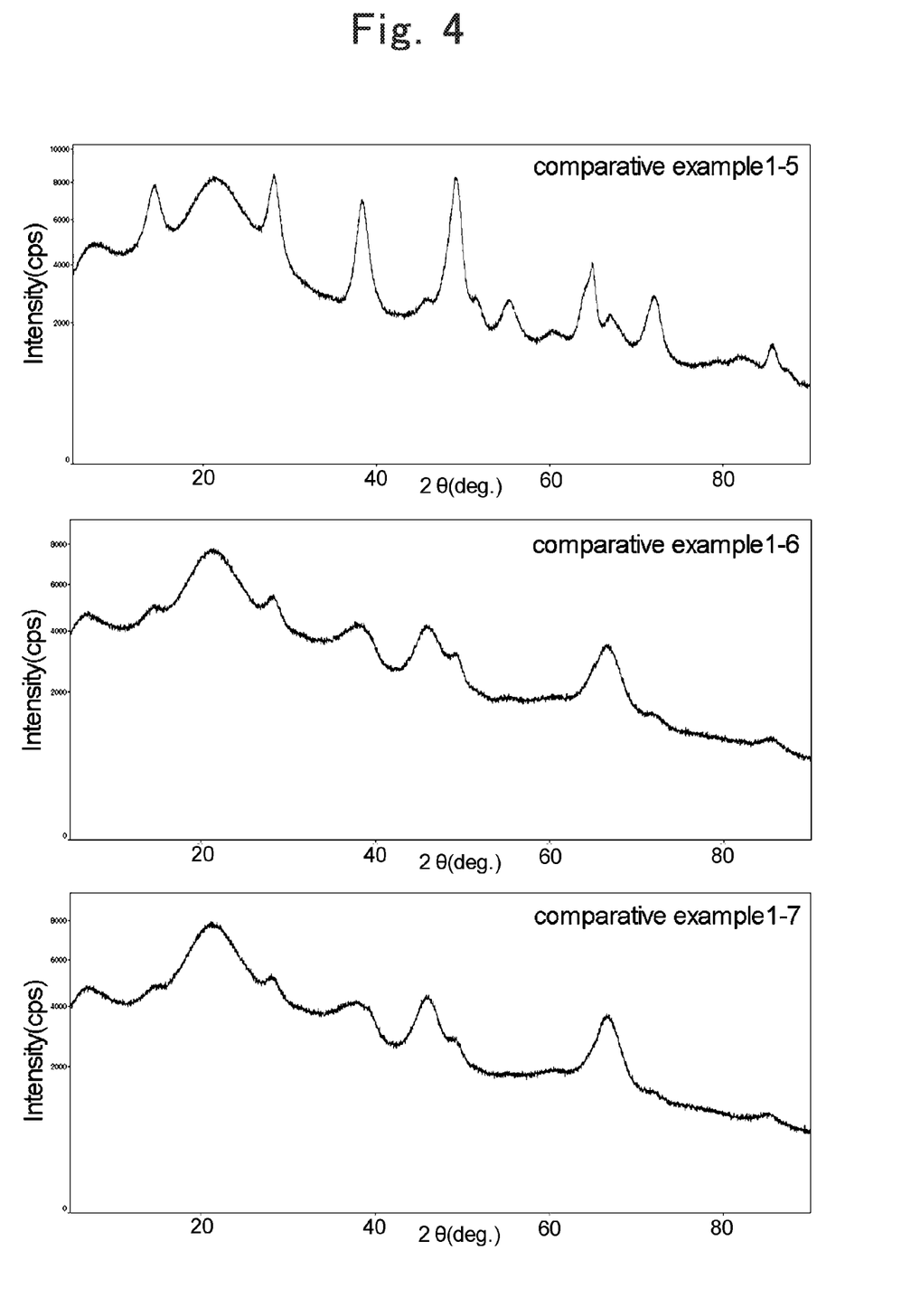
FIG. 4 illustrates an XRD spectrum of each sample in comparative examples.

Table 7 indicates the specific surface area, the refractive index, and the result of XRD for the particle material of each comparative example. FIG. 2 shows an XRD spectrum measured for each of comparative examples 1-0, 1-1, 1-3, and 1-4. FIG. 4 shows an XRD spectrum measured for each of comparative examples 1-5 to 1-7.

TABLE 7

| Comparative example | Mean particle diameter (μm) | Specific surface area (m²/g) | Refractive index | 2θ | FWHM | 2θ | FWHM | Heating temperature (° C.) |
|---|---|---|---|---|---|---|---|---|
| 1-0 | 1.7 | 342.1 | 1.56 | 49.4 | 1.6 | 64.9 | 1.1 | 160 |
| 1-1 | 1.7 | 204.7 | 1.63 | 46.1 | 2.1 | 66.7 | 2 | 160-650 |
| 1-2 | 1.6 | 180 | 1.64 | 45.8 | 1.8 | 66.7 | 1.9 | 160-850 |
| 1-3 | 1.5 | 64.1 | 1.66 | 45.6 | 2.7 | 66.5 | 0.3 | 160-850-1100 |
| 1-4 | 0.9 | 3.3 | — | 46.2 | 0.2 | 66.5 | 0.2 | 160-850-1200 |
| 1-5 | 1.7 | 340 | 1.60 | 45.8 | 0.9 | 64.8 | 1.5 | 160-250 |
| 1-6 | 1.7 | 200 | 1.63 | 45.8 | 4.6 | 66.8 | 3.8 | 160-400 |
| 1-7 | 1.7 | 200 | 1.65 | 45.7 | 3.7 | 66.9 | 3.5 | 160-450 |

As is apparent from Table 7 since the surface did not have a layer formed of silica, fusion of the primary particles progressed by heating, and the specific surface area was reduced and the primary particles swelled. Therefore, transmissivity of light rays was influenced by the swelling of the particles. Furthermore, in comparative example 1-4 in which heating was performed at 1200° C., the half-value width of a peak appearing at 2θ of each of 45° to 49° and 64° to 67° in a spectrum measured by XRD was 0.2°, and transition of γ alumina to α alumina occurred. As a result, the specific surface area was reduced and the particles swelled. Thus, the result indicated that transition to α alumina by heating was inhibited by generating a layer formed of silica on the surface formed of boehmite.

(Test 6)

10 parts by mass of the particle material (refractive index=1.54) of example 2-2 and 100 parts by mass of two-component silicone OE-6631 (refractive index=1.54, light transmittance (450 nm/1 mm)=100%) manufactured by Toray Dow Corning were mixed by a rotation-revolution mixer to obtain a thermally-cured product of silicone. The thermally-cured product of silicone was put in a mold having a thickness of 2 mm, and heated at 150° C. for one hour and hardened. The light transmittance of the hardened piece was measured and indicated 99% (400 nm/2 mm). As to a strength, the tensile strength was 1.5 based on the strength of the resin only being 1.

(Test 7)

20 parts mass of the particle material (refractive index=1.52) of example 2-2 and 100 parts by mass of a commercially available clear coating material (refractive index after hardening=1.51) formed of hydroxy-group-containing acrylic resin/butyl-etherified melamine resin were mixed by a Disper to obtain a clear coating material. A coating film was formed on a surface of a plate glass so as to obtain a 30 μm coating film.

A clear film was obtained through baking at 145° C. for 30 minutes. The light transmittance of the film was measured and indicated 99.8% (400 nm/30 μm). In this case, the light transmittance calculated for the film thickness of 2 mm was 87%. As to the strength, the tensile strength was 1.2 based on strength of the resin only being 1.

(Test 8)

30 parts by mass of the particle material (refractive index=1.52) of example 2-3 and 100 parts by mass of LE 1421 (two component type, refractive index 1.51) manufactured by Sanyu Rec Co., Ltd were mixed and formed into a plate having a thickness of 300 μm.

The hardening conditions were 80° C. for one hour+120° C. for one hour. The light transmittance of the plate was measured and indicated 97% (400 nm/300 μm). In this case, the light transmittance calculated for the film thickness of 2 mm was 82%. The flexural modulus of elasticity was 1.4 based on the elastic modulus of the resin only being 1.

(Test 9)

20 parts by mass of the particle material (refractive index=1.59) of example 2-1 and 100 parts by mass of commercially available polycarbonate were kneaded by a kneader to obtain pellets.

A test piece having a thickness of 2 mm was produced through injection molding. The light transmittance was measured and indicated 95%. The flexural modulus of elasticity was 1.2 based on the elastic modulus of the resin only being 1.

(Test 10)

20 parts by mass of a particle material (refractive index=1.490) obtained by treating the particle material of example 4-5 with methyltrimethoxysilane and 100 parts by mass of commercially available polymethylmethacrylate were kneaded by kneader to obtain pellets. A test piece having a thickness of 2 mm was produced through injection molding. The light transmittance was measured and indicated 98%. As to the strength, the bending strength was 1.2 based on the elastic modulus of the resin only being 1.

(Test 11)

30 parts by mass of the particle material (refractive index=1.59) of example 2-1 and 100 parts by mass (in terms of solid content) of transparent PI type A (refractive index=1.60) manufactured by Mitsubishi Chemical Corporation were mixed to form a film having a thickness of 100 μm through casting.

The light transmittance of the film was measured and indicated 99% (400 nm/100 μm). In this case, the light transmittance calculated for the film thickness of 2 mm was 82%. The bending strength was 1.1 based on the elastic modulus of the resin only being 1.

(Test 12)

A coating film was produced in the same manner as in Test 7 except that the particle material of example 2-2 was treated with 3% by mass of glycidylpropyitrimethoxysilane with respect to the mass of the particle material. The light transmittance of the film was 98% (400 nm/300 μm) and the tensile strength was enhanced by 20% as compared with Test 7. The light transmittance of the film calculated for the film thickness of 2 mm was 87%. The bending strength was 1.4 based on the elastic modulus of the resin only being 1.

(Test 13)

30 parts by mass of the particle material (refractive index=1.42) of example 4-7 and 100 parts by mass of silicone resin (two-component type: CELVENUS A1070 manufactured by Daicel Corporation (refractive index=1.41)) were mixed by a rotation-revolution mixer, put in a mold having a thickness of 2 mm, and heated at 80° C. for one hour and 150° C. for four hours to be hardened. The light transmittance of the hardened piece was measured and indicated 92% (400 nm/2 mm). The tensile strength was 1.6 based on the strength of the resin only being 1.

(Test 14)

A test piece was produced in the same manner as in Test 6 by using the particle material of comparative example 1-2, and the light transmittance was measured. As a result, the light transmittance calculated for the film thickness of 2 mm was less than 10%, and the test piece was not transparent. The tensile strength was 1.5 based on that of the resin material being 1.

(Test 15)

A test piece was produced in the same manner as in Test 8 by using the particle material of comparative example 1-4 and the light transmittance was measured. As a result, the light transmittance calculated for the film thickness of 2 mm was less than 10%, and the test piece was not transparent. Influence of scattering of light rays by swelling of particles due to transition to α alumina was assumed to be exerted. The flexural modulus of elasticity was 1.6.

(Tests 16 to 22)

Test pieces of Tests 14 to 22 were produced in the same manners as in Tests 6, 8, 6 to 11, and 13, respectively, except that a particle material was produced with gel-process silica (SYLYSIA manufactured by Fuji Silysia Chemical Ltd.: specific surface area 285 m²/g). The light transmittance and the strength (tensile strength or bending strength) were measured. The results are indicated in Table 8.

TABLE 8

|  |  | Transparent resin materal | Particle material | Transmittance Calculated for thickness of 2 mm | Evaluation | Strength data | | Basis of test |
|---|---|---|---|---|---|---|---|---|
|  |  |  |  |  |  | Strength based on that of resin being 1 | Type of strength |  |
| Example | Test 6 | silicone resin | Example 2-2 | 99 | transparent | 1.5 | tensile strength |  |
|  | Test 7 | acrylic melamine resin coating material | Example 2-3 | 87 | transparent | 1.2 | tensile strength |  |
|  | Test 8 | epoxy resin | Example 2-3 | 82 | transparent | 1.4 | flexural modulus of elasticity |  |
|  | Test 9 | polycarbonate | Example 2-1 | 95 | transparent | 1.2 | flexural modulus of elasticity |  |
|  | Test 10 | polymethyl-methacrylate | Example 4-5 | 98 | transparent | 1.2 | flexural modulus of elasticity |  |
|  | Test 11 | polyimide | Example 2-1 | 82 | transparent | 1.1 | tensile strength |  |
|  | Test 12 | acrylic melamine resin coating material | Example 2-2 | 87 | transparent | 1.4 | tensile strength |  |
|  | Test 13 | silicone resin | Example 4-7 | 92 | transparent | 1.6 | tensile strength |  |
| Comparative example | Test 14 | silicone resin | Comparative example 1-2 | <10 | imperfectly transparent | 1.5 | tensile strength | Test 6 |
|  | Test 15 | epoxy resin | Comparative example 1-4 | <10 | imperfectly transparent | 1.6 | flexural modulus of elasticity | Test 8 |
|  | Test 16 | silicone resin | gel-process silica | 35 | imperfectly transparent | 1.6 | tensile strength | Test 6 |
|  | Test 17 | acrylic melamine resin coating material | gel-process silica | <10 | imperfectly transparent | 1.3 | tensile strength | Test 7 |
|  | Test 18 | epoxy resin | gel-process silica | <10 | imperfectly transparent | 1.5 | flexural modulus of elasticity | Test 8 |
|  | Test 19 | polycarbonate | gel-process silica | <10 | imperfectly transparent | 1.3 | flexural modulus of elasticity | Test 9 |
|  | Test 20 | polymethyl-methacrylate | gel-process silica | 74 | imperfectly transparent | 1.3 | flexural modulus of elasticity | Test 10 |
|  | Test 21 | polyimide | gel-process silica | <10 | imperfectly transparent | 1.2 | tensile strength | Test 11 |
|  | Test 22 | silicone resin | gel-process silica | 65 | imperfectly transparent | 1.6 | tensile strength | Test 13 |

As is apparent from Table 8, for the particle material (comparative examples 1-2 and 1-4: Test examples 14 and 15) that did not have a silica layer on the surface and was thus swelled by heating, and for an aggregate of silica (gel-process silica: Test examples 16 to 22) which was conventionally used, although strength was enhanced to some degree by dispersion in the resin, the transparency was not sufficient.

(Additional Test and Examination)

Products of examples 5-1 to 5-3 were each produced by adding both TEOS and colloidal silica by amounts indicated in Table 9 when the particle material of example 4-1 was produced. A product of comparative example 5-1 was produced by adding colloidal silica by an amount indicated in Table 9 without adding TEOS when the particle material of example 4-1 was produced.

TABLE 9

| | Specific surface area diameter (nm) | Boehmite (parts by mass) | Blending amount of TEOS (parts by mass) | Blending amount of colloidal silica (parts by mass) | Refractive index | Boehmite:silica (theoretical ratio) |
|---|---|---|---|---|---|---|
| Example | | | | | | |
| 5-1 | 7 | 100 | 20 | 2 | 1.56 | 54:46 |
| 5-2 | 7.7 | 100 | 20 | 4 | 1.54 | 50:50 |
| 5-3 | 8.1 | 100 | 20 | 6 | 1.51 | 38:62 |
| Comparative Example | | | | | | |
| 5-1 | 7 | 100 | 0 | 4 | Measurement was impossible | 63:37 |

As is apparent from the table, in a case where TEOS was added, transparency was maintained (measurement of the refractive index was possible) even when colloidal silica was added. In comparative example 5-1, pores that did not communicate with the outside were generated, and, thus, the measurement of the refractive index was assumed to become impossible.

(Additional Examination)

Transition of boehmite to γ alumina occurs by heating boehmite at a high temperature. Therefore, influence of silica in the surface on the transition from boehmite to γ alumina was examined by examining the generation and loss.

Figure 5:
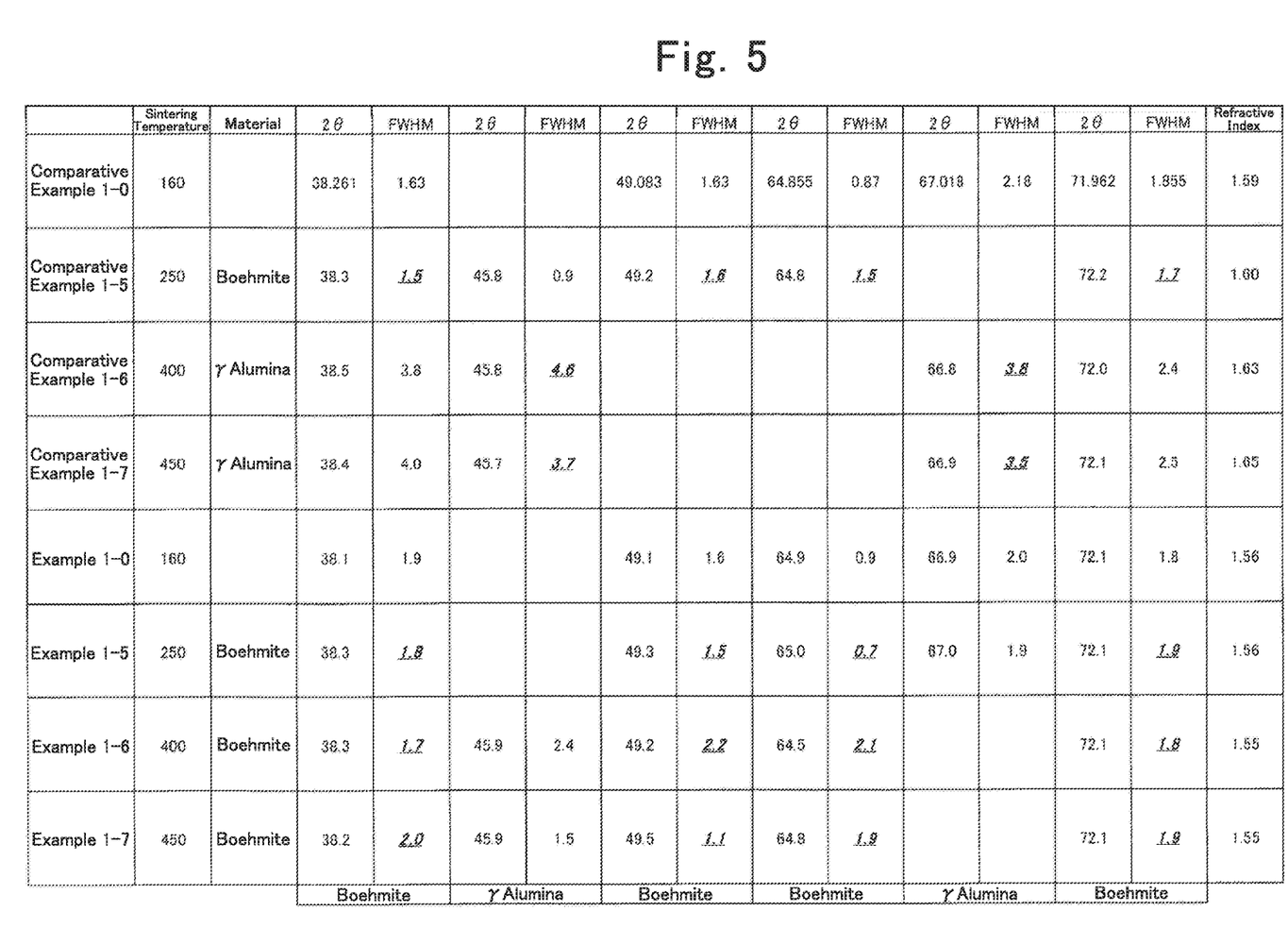
FIG. 5 illustrates a result of analysis of the XRD spectrum of each sample in examples and comparative examples.

Specifically, based on the results shown in FIGS. 3 and 4, loss of boehmite and generation of γ alumina were analyzed, and influence of presence or absence of silica in the surface and change of the heating temperature was examined. Each of peaks appearing near 2θ of 38°, 50°, 64°, and 72° was derived from boehmite, and each of peaks appearing near 2θ of 45° and 67° was derived from γ alumina. In a case where all the peaks derived from boehmite as described above appeared, and the half-value width (FWHM) of each of all the peaks was narrow (for example, not greater than 2.5°, and preferably not greater than 0.5°), boehmite was determined as being contained as a main component. In a case where all the peaks derived from γ alumina as described above appeared and the half-value width of each of all the peaks was not less than 0.5° (preferably not less than 3.0°), a substantial amount of γ alumina was determined to have been generated. FIG. 5 shows the analysis results.

Each of the samples in these tests was originally formed of boehmite only and did not substantially contain γ alumina. Therefore, in a case where a peak derived from γ alumina was observed based on the above-described criterion, transition from boehmite to γ alumina is determined to have progressed. Furthermore, the refractive index of each of these samples was measured, and is also shown in FIG. 5.

As is apparent from FIG. 5, in comparative example 1-5 in which heating was performed at 250° C., a peak derived from γ alumina was small and boehmite was a main component. However, as in comparative example 1-6 in which heating was performed at 400° C., and in comparative example 1-7 in which heating was performed at 450° C., transition to γ alumina is determined to have occurred according to increase of the heating temperature. The transition to γ alumina caused increase of the refractive index.

Meanwhile, in examples 1-5 to 1-7 in which the surface was formed of silica, boehmite was a main component and generation of γ alumina was not substantially observed even when heating was performed at 250° C. (example 1-5), 400° C. (example 1-6), and 450° C. (example 1-7). The refractive index did not greatly vary. The heating was performed at a high temperature and binding particle materials was made strong while boehmite was maintained.

Figure 6:
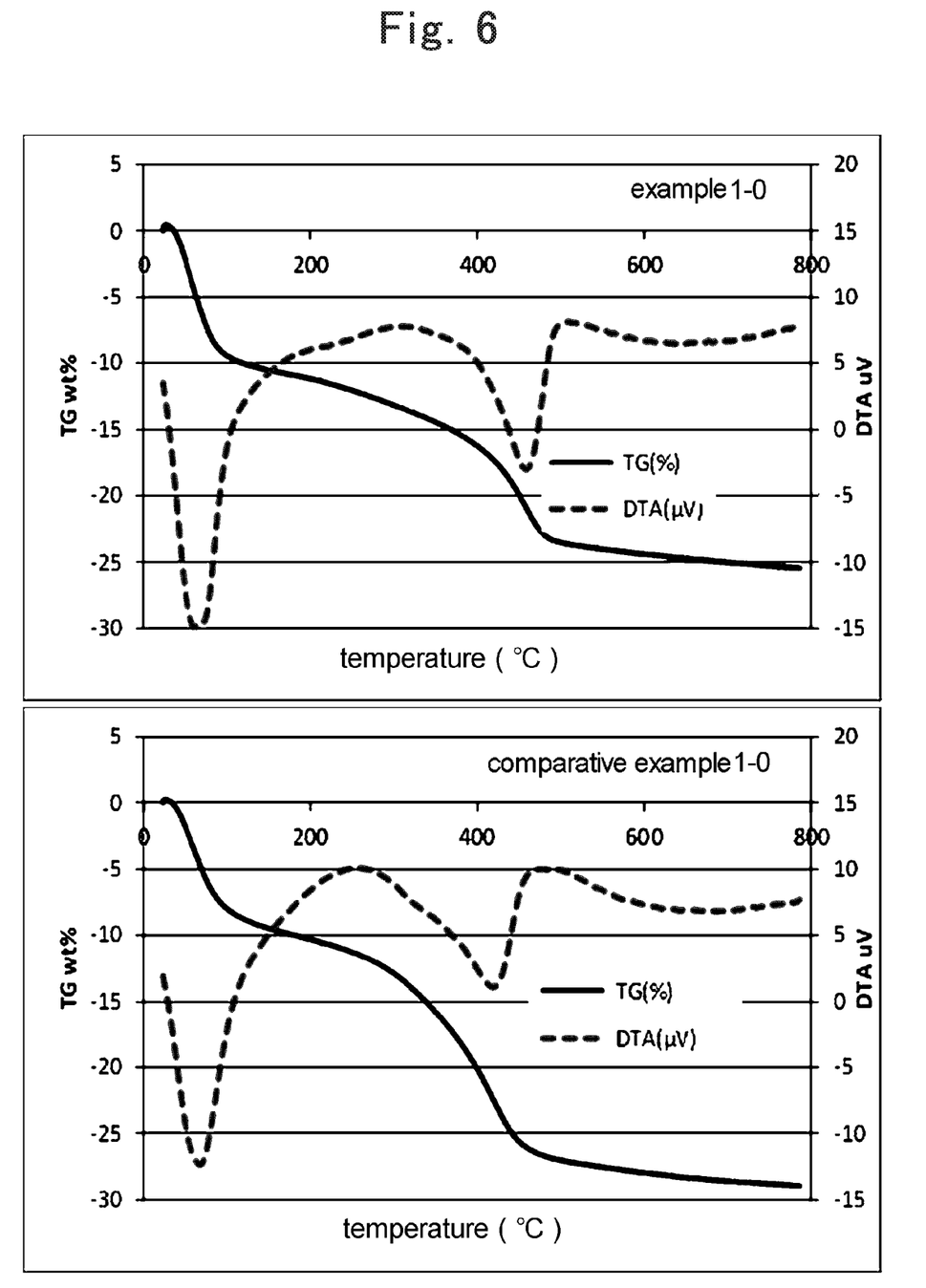
FIG. 6 illustrates a result of TG-DTA measurement of each sample in example 1-0 and comparative example 1-0.

For reference, FIG. 6 shows results of TG-DTA measurement for example 1-0 and comparative example 1-0. The sample of example 1-0 had an endothermic peak near 460° C., and transition of boehmite to γ alumina is determined to have occurred near this temperature. Meanwhile, the sample of comparative example 1-0 had an endothermic peak near 420° C., and this temperature was 40° C. lower than the temperature indicating the endothermic peak in example 1-0 in which the surface was formed of silica.

(Others: Application of the Particle Material and the Transparent Resin Composition According to the Present Embodiment Described Above)

An example of application of the particle material and the transparent resin composition according to the present embodiment will be described below. In the following description, description made so as to limit a transparent resin material for the transparent resin composition is for illustrating a preferable resin, and is not intended to make a limitation that only the resin material is usable.

In a case where the transparent resin material for the transparent resin composition is epoxy resin or silicone resin, the transparent resin composition is preferably used for the transparent resin composition for sealing an optical device. Examples of the optical device include an LED, an optical sensor, and a light guide. A high transparency, a low CTE, a high gas barrier property, a high elastic modulus, and the like are expected.

In a case where the transparent resin material for the transparent resin composition is acrylic resin, the transparent resin composition is preferably used for a resin composition for a dental material. The composition for a dental material is applicable to a dental restoring material such as an artificial tooth and a prosthesis. A high transparency, a low coefficient of thermal expansion (CTE), a high elastic modulus, a high surface hardness, a high compression strength, and the like are expected.

In a case where the transparent resin material for the transparent resin composition is polyimide, polyester, or epoxy resin, the transparent resin composition is preferably used for a transparent film. A high transparency, a high gas barrier property, a high surface hardness, a high antiblocking property, and the like are expected. The transparent film is applicable to, for example, electronic devices such as displays (for example, resin glass for a display, a film for a display substrate), and to wrapping for enhancing designs.

In a case where the particle material is contained in a design layer, the particle material is preferably applied to decorative film for insert molding, in-molding, or the like. The design layer is allowed to contain a pigment, dye, or the like in addition to the particle material of the present embodiment. A high transparency, a high gas barrier property, a high surface hardness, and the like are expected. In order to form the design layer, the particle material of the present embodiment is dispersed in a dispersion medium (for example, transparent resin material as described above). Furthermore, a pigment, a dye, metal particles, or a metal foil is allowed to be contained for coloring. For example, a decorative film is integrated with an object through thermal transfer.

In a case where the particle material is contained in an oil vehicle, the particle material is preferably applied to an oil transparent coating composition. A high transparency, a low CTE, a high surface hardness, and the like are expected.

The transparent resin composition is used for an optical lens, whereby a high transparency, a low CTE, a high surface hardness, and the like are expected.

An optical adhesive composition formed of the transparent resin composition of the present embodiment is provided. An unpolymerized precursor is mixed as the transparent resin material to be contained and is hardened by heat and light as necessary, or the transparent resin composition of the present embodiment is dissolved in a proper solvent and is hardened through transpiration of the solvent. A high transparency and a low CTE are achieved. The optical adhesive composition is preferably used for adhering optical components. The optical adhesive composition is also applicable to an optical display and the like.

A resin glass molded product formed of the transparent resin composition of the present embodiment is provided. A high transparency, a low CTE, a high elastic modulus, a high surface hardness, and the like are achieved.

A mobile communication terminal housing formed of the transparent resin composition the present embodiment is provided. The housing has millimeter wave transmissivity. Since the particle size of the primary particle of the particle material to be contained is small, absorption of a millimeter wave is reduced. In a case where a mobile information device or the like is used as the mobile communication terminal, high-speed communication is achieved. Furthermore, a millimeter wave radar for a moving body such as an automobile is also used as the mobile communication terminal. A high transparency, a surface hardness, and the like are achieved.

In a case where a molded product obtained by molding the transparent resin composition of the present embodiment has a slanted structure in which a content of the particle material of the present embodiment increases toward the surface, a high transparency, a low CTE, a high surface hardness, and the like are expected. A method for achieving the slanted structure is not particularly limited. However, for example, a method in which a molded product is formed from materials having different contents of the particle material (a content of the particle material is made different for each portion of the molded product by using in-molding or the like), is used. Either thermosetting resin or thermoplastic resin is used for the resin composition. The molded product is not particularly limited, and is used for the above-described usages. By increasing the content of the particle material in the surface, the properties of the surface are improved by the particle material. Since the particle material is collected in the surface, improvement of a gas barrier property and a surface hardness is particularly expected.

The surface of a molded product obtained by molding the transparent resin composition of the present embodiment is allowed to have a projecting and recessed structure that contains the particle material. In a case where the molded product is formed by using a mold or the like, the projecting and recessed structure is formed by transferring a projecting and recessed structure formed in the surface of the mold, or the projecting and recessed structure is formed by depositing the particle material on the surface. A particle structure is included in the projecting and recessed structure. A high transparency, a low CTE, a high gas barrier property, a high surface hardness, a high antiblocking property, and the like are expected. Either thermosetting resin or thermoplastic resin is used for the resin composition. The molded product is not particularly limited, and is used for the above-described usages.

What is claimed is:

1. A particle material comprising
   an aggregate used so as to be dispersed in a transparent resin material,
   the aggregate including primary particles in which a specific surface area diameter based on a surface communicating with outside air is not less than 0.8 nm and not greater than 80 nm, wherein each of the primary particles is formed of an inorganic substance in which a composition of a surface and a composition of an inside are different from each other,
   the aggregate being formed by binding and fusing the primary particles through dehydration and condensation, wherein a volume average particle diameter of the aggregate is greater than 0.1 µm,
   the composition of the surface has a refractive index different from that of the composition of the inside,
   an existence ratio between the composition of the surface and the composition of the inside is determined such that a hardened product which is obtained by dispersing and hardening 10 parts by mass of the aggregate in 100 parts by mass of the transparent resin material,
   the primary particles each have the inside formed of boehmite or γ alumina and the surface formed of silica, and
   the particle material does not include a particle material in which a volume average particle diameter is not less than 6 nm and not greater than 0.2 µm.

2. A particle material comprising
   an aggregate used so as to be dispersed in a transparent resin material,
   the aggregate including primary particles in which a specific surface area diameter based on a surface communicating with outside air is not less than 0.8 nm and not greater than 80 nm, wherein each of the primary particles is formed of an inorganic substance in which a composition of a surface and a composition of an inside are different from each other,
   the aggregate being formed by binding and fusing the primary particles through dehydration and condensation, wherein a volume average particle diameter of the aggregate is greater than 0.1 µm, the composition of the surface has a refractive index different from that of the composition of the inside,
   an existence ratio between the composition of the surface and the composition of the inside is determined such that a hardened product which is obtained be dispersing and hardening 10 parts by mass of the aggregate in 100 parts by mass of the transparent resin material, the primary particles each have the inside formed of boehmite or 7 alumina and the surface formed of silica, and the aggregate also includes second particles formed of an oxide of an element that has an atomic number of 38 or higher.

3. The particle material according to claim 1, wherein the volume average particle diameter in the aggregate is not less than 0.5 μm and not greater than 500 μm.

4. The particle material according to claim 2, wherein the volume average particle diameter in the aggregate is not less than 0.5 μm and not greater than 500 μm.

5. The particle material according to claim 1, comprising a coating layer formed of an organic substance for covering surfaces of the primary particles, wherein the coating layer binds to the surfaces of the primary particles through covalent bond or by an intermolecular force.

6. The particle material according to claim 2, comprising a coating layer formed of an organic substance for covering surfaces of the primary particles, wherein the coating layer binds to the surfaces of the primary particles through covalent bond or by an intermolecular force.

7. The particle material according to claim 5, wherein the organic substance is a condensation product of a silane compound.

8. The particle material according to claim 6, wherein the organic substance is a condensation product of a silane compound.

9. A manufacturing method for manufacturing the particle material according to claim 1, the manufacturing method comprising:

a dispersing step of dispersing, in a liquid dispersion medium, core particles which constitute inside composition of the primary particles, wherein the inside composition is formed of γ alumina, to form a dispersion liquid;

a coating step of adding a coating composition comprising a silica precursor formed of a silane compound, a colloidal silica, or both to the dispersion liquid, to coat the core particles with the coating composition, thereby forming coated particles; and an aggregating step of forming an aggregate by heating the coated particles up to a temperature of not lower than 900° C., thereby subjecting the coated particles to dehydration and condensation to bind and fuse the coated particles, and form silica as the composition on the surface of the primary particles.

10. A manufacturing method for manufacturing the particle material according to claim 1, the manufacturing method comprising:

a dispersing step of dispersing, in a liquid dispersion medium, core particles which constitute inside composition of the primary particles, wherein the inside a composition is formed of boehmite, to form a dispersion liquid;

a coating step of adding a coating composition comprising a silica precursor formed of a silane compound, a colloidal silica, or both to the dispersion liquid, to coat the core particles with the coating composition, thereby forming coated particles; and an aggregating step of forming an aggregate by heating the coated particles up to a temperature of not lower than 250° C., thereby subjecting the coated particles to dehydration and condensation to bind and fuse the coated particles, and form silica as the composition on the surface of the primary particles.

11. The manufacturing method according to claim 9, further comprising a modifying step of bringing a silane compound into contact with the surfaces of the coated particles obtained in the coating step.

12. The manufacturing method according to claim 10, further comprising a modifying step of by bringing a silane compound into contact with the surfaces of the coated particles obtained in the coating step.

13. A transparent resin composition comprising:
the particle material according to claim 1; and
a transparent resin material in which the particle material is dispersed.

14. A transparent resin composition comprising:
the particle material according to claim 2; and
a transparent resin material in which the particle material is dispersed.

15. A transparent resin composition comprising:
the particle material according to claim 7; and
a transparent resin material in which the particle material is dispersed.

16. A transparent resin composition comprising:
the particle material according to claim 8; and
a transparent resin material in which the particle material is dispersed.

* * * * *

UNITED STATES PATENT AND TRADEMARK OFFICE
CERTIFICATE OF CORRECTION

| | | |
|---|---|---|
| PATENT NO. | : 11,976,179 B2 | Page 1 of 1 |
| APPLICATION NO. | : 17/005619 | |
| DATED | : May 7, 2024 | |
| INVENTOR(S) | : Kenta Hori et al. | |

It is certified that error appears in the above-identified patent and that said Letters Patent is hereby corrected as shown below:

On the Title Page

In item (30), "PCT/JP2019/008389" should read as --PCT/JP2018/008060--.

Signed and Sealed this
Eighth Day of October, 2024

Katherine Kelly Vidal
*Director of the United States Patent and Trademark Office*